United States Patent

Matsumoto et al.

(12) 
(10) Patent No.: US 6,489,081 B1
(45) Date of Patent: Dec. 3, 2002

(54) ORGANOSILYL RADICAL GENERATORS AND THEIR APPLICATIONS

(75) Inventors: Akira Matsumoto, Amagasaki (JP); Yoshihiko Ito, Kyoto (JP)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 224 days.

(21) Appl. No.: 09/726,684

(22) Filed: Nov. 30, 2000

(51) Int. Cl.[7] .............................. C07F 5/02; G03F 7/029
(52) U.S. Cl. .................... 430/281.1; 430/325; 556/402; 540/4; 544/69; 544/229; 522/26; 522/28; 522/63; 522/65; 548/110; 548/405; 546/13
(58) Field of Search .............................. 430/281.1, 325; 556/402; 540/4; 544/69, 229; 546/13; 548/110, 405; 522/26, 28, 63, 65

(56) References Cited

FOREIGN PATENT DOCUMENTS

| JP | 4-107462 A | * | 4/1992 |
| JP | 1143492 | | 11/1999 |

OTHER PUBLICATIONS

C. Chatgilialoglu, Acc. Chem. Res., (1992), vol. 25, pp. 188–194.
C. Chatgilialoglu, Chem. Rev., (1995), vol. 95, pp. 1229–1251.
M. Steinmetz, Chem. Rev., (1995), vol. 95, pp. 1527–1588.
A. Matsumoto et al., J. Org. Chem. (2000), vol. 65, No. 18, pp. 5707–5711.
Beilstein InformationssytemeGmbH, Chem. Ber. 99, (1966), pp. 2197–2205, (abstract).
Shun–Ya Onozawa et al., Chem. Commun. (1997), vol. 13, pp. 1229–1230.
Chem. Abstr. vol. 97, No. 7, (1982), No. 52379 for Liebigs Ann. Chem. (1981), vol. 11, pp. 2067–2080.
Abstract for JP 11043492 (1999).

* cited by examiner

Primary Examiner—John A. McPherson
(74) Attorney, Agent, or Firm—Tyler A. Stevenson

(57) ABSTRACT

Compounds of formula I

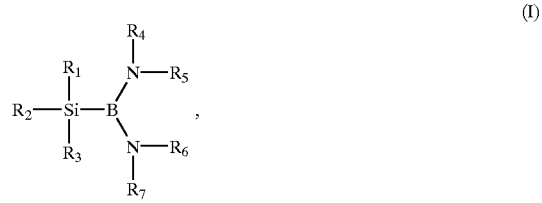

wherein $R_1$, $R_2$, and $R_3$ independently of one another are hydrogen; $C_1$–$C_{20}$alkyl which is unsubstituted or substituted by OH, $C_1$–$C_4$alkoxy, $C_1$–$C_4$alkylthio, phenylthio, F, Cl, Br, I, CN, ($C_1$–$C_8$alkyl)O—(CO)—, ($C_1$–$C_4$alkyl)—(CO)O— or/and di($C_1$–$C_4$alkyl)amino; or $R_1$, $R_2$, and $R_3$ independently of one another are $C_3$–$C_6$alkenyl; phenyl which is unsubstituted or substituted by OH, $C_1$–$C_4$alkoxy, $C_1$–$C_4$alkylthio, phenylthio, F, Cl, Br, I, CN, ($C_1$–$C_8$alkyl)O(CO)—, ($C_1$–$C_4$alkyl)—(CO)O— or/— and di($C_1$–$C_4$alkyl)amino; or $R_1$ and $R_2$ together are $C_2$–$C_9$alkylene, o-xylylene, 2-butenylene, $C_3$–$C_9$oxaalkylene or $C_3$–$C_9$azaalkylene; $R_4$, $R_5$, $R_6$, and $R_7$ independently of one another are sec-$C_3$–$C_{20}$alkyl, tert-$C_4$–$C_{20}$alkyl or phenyl wherein these radicals are unsubstituted or substituted by OH, $C_1$–$C_4$alkoxy, $C_1$–$C_4$alkylthio, phenylthio, F, Cl, Br, I, CN, ($C_1$–$C_8$alkyl)O(CO)—, ($C_1$–$C_4$alkyl)—(CO)O— or/and di($C_1$–$C_4$alkyl)amino; or $R_4$ and $R_5$, and/or $R_6$ and $R_7$ together are $C_2$–$C_9$alkylene, o-xylylene, 2-butenylene, $C_3$–$C_9$oxaalkylene or $C_3$–$C_9$azaalkylene, or $R_4$ and $R_6$, and/or $R_5$ and $R_7$ together are branched $C_2$–$C_9$alkylene, o-xylylene, 2-butenylene, $C_3$–$C_9$oxaalkylene or $C_3$–$C_9$azaalkylene; are suitable as photoinitiators for the photopolymerization of unsaturated compounds.

11 Claims, No Drawings

ORGANOSILYL RADICAL GENERATORS AND THEIR APPLICATIONS

The present application refers to novel compounds generating organosilyl radicals upon irradiation with light, and to the use of thus generated organosilyl radicals for various chemical reactions such as for example polymerization.

In Acc. Chem. Res. Vol. 25, 188–194 (1992) and Chem. Rev. Vol. 95, 1229–1251 (1995), various applications of organosilyl radicals are disclosed. However, the methods of generating organosilyl radicals are still limited. For instance, organosilyl radicals can be generated by treatment of organosilyl hydride with conventional radical initiators such as for example benzoyl peroxide as described in Chem. Rev. Vol. 95, 1229–1251 (1995), or by photolysis of poly(organosilane)s as is disclosed in Chem. Rev. Vol. 95, 1527–1588 (1995).

In technique radicals useful for initiating chemical reactions, especially polymerization reactions, are needed.

Subject of this invention therefore are novel compounds of formula 1, which generate organosilyl radicals by irradiation of light and

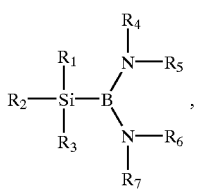

(I)

$R_1$, $R_2$, and $R_3$ independently of one another are hydrogen; $C_1$–$C_{20}$alkyl which is unsubstituted or substituted by OH, $C_1$–$C_4$alkoxy, $C_1$–$C_4$alkylthio, phenylthio, F, Cl, Br, I, CN, ($C_1$–$C_8$-alkyl)O(CO)—, ($C_1$–$C_4$alkyl)-(CO)O— or/and di($C_1$–$C_4$alkyl)amino; or $R_1$, $R_2$, and $R_3$ independently of one another are $C_3$–$C_6$alkenyl; or are phenyl which is unsubstituted or substituted by OH, $C_1$–$C_4$alkoxy, $C_1$–$C_4$alkylthio, phenylthio, F, Cl, Br, I, CN, ($C_1$–$C_8$alkyl)O(CO)—, ($C_1$–$C_4$alkyl)-(CO)O— or/and di($C_1$–$C_4$alkyl)amino; or $R_1$ and $R_2$ together are $C_2$–$C_9$alkylene, o-xylylene, 2-butenylene, $C_3$–$C_9$oxaalkylene or $C_3$–$C_9$azaalkylene;

$R_4$, $R_5$, $R_6$, and $R_7$ independently of one another are sec-$C_3$–$C_{20}$alkyl, tert-$C_4$–$C_{20}$alky or phenyl wherein these radicals are unsubstituted or substituted by OH, $C_1$–$C_4$alkoxy, $C_1$–$C_4$alkylthio, phenylthio, F, Cl, Br, I, CN, ($C_1$–$C_8$alkyl)O(CO)—, ($C_1$–$C_4$alkyl)-(CO)O— or/and di($C_1$–$C_4$alkyl)amino;

or $R_4$ and $R_5$, and/or $R_6$ and $R_7$ together are $C_2$–$C_9$alkylene, o-xylylene, 2-butenylene, $C_3$–$C_9$oxaalkylene or $C_3$–$C_9$azaalkylene, or $R_4$ and $R_6$, and/or $R_5$ and $R_7$ together are branched $C_2$–$C_9$alkylene, o-xylylene, 2-butenylene, $C_3$–$C_9$oxaalkylene or $C_3$–$C_9$azaalkylene.

$C_1$–$C_{20}$alkyl is linear or branched and is, for example, $C_1$–$C_{18}$—, $C_1$–$C_{14}$—, $C_1$–$C_{12}$—, $C_1$–$C_8$—, $C_1$–$C_6$— or $C_1$–$C_4$alkyl. Examples are methyl, ethyl, propyl, isopropyl, n-butyl, sec-butyl, isobutyl, tertbutyl, pentyl, hexyl, heptyl, 2,4,4-trimethylpentyl, 2-ethylhexyl, octyl, nonyl, decyl, dodecyl, tetradecyl, pentadecyl, hexadecyl and octadecyl.

sec-$C_3$–$C_{20}$alkyl is branched $C_3$–$C_{20}$alkyl, for example, isopropyl, sec-butyl.

tert-$C_3$–$C_{20}$alkyl is branched $C_3$–$C_{20}$ alkyl, for example, tert-butyl, tert-amyl.

$C_2$–$C_9$alkylene is linear or branched alkylene, for example $C_2$–$C_7$alkylene, $C_2$–$C_6$alkylene, $C_2$–$C_4$alkylene, namely, ethylene, propylene, 1-methylethylene 1,1-dimethyl-ethylene, 2,2-dimethylpropylene, butylene, 1-methylbutylene, 1-methylpropylene, 2-methyl-propylene, pentylene, hexylene, heptylene, octylene, or nonylene.

$C_3$–$C_9$oxaalkylene is linear or branched $C_3$–$C_9$alkylene, having a meaning as defined above and being interrupted by one or more, e.g. 1–6, 1–5, 1–4 or 1, 2, or 3, non-successive O atoms. $C_3$–$C_9$oxaalkylene for example, produces structural units such as —$CH_2CH_2$—O—$CH_2$—, —$CH_2CH_2$—O—$CH_2CH_2$—, —[$CH_2CH_2$O]$_y$—, —[$CH_2CH_2$O]$_y$—$CH_2$—, where y=1–4, —($CH_2CH_2$O)$_3CH_2CH_2$—, —$CH_2$—CH($CH_3$)—O—$CH_2$—CH($CH_3$)— or —$CH_2$—CH($CH_3$)—O—$CH_2$—$CH_2CH_2$—.

$C_3$–$C_9$azaalkylene is linear or branched $C_3$–$C_9$alkylene as described above, which is interrupted by one or more, e.g. 1–6, 1–5, 1–4 or 1, 2, or 3 N-atoms. $C_3$–$C_9$azaalkylene produces, for example, structural units such as —$CH_2CH_2$—NH—$CH_2$—, —$CH_2CH_2$—N($CH_3$)—$CH_2$—, —$CH_2CH_2$—NH—$CH_2CH_2$—, —$CH_2CH_2$—N($CH_3$)—$CH_2CH_2$—, —[$CH_2CH_2$NH]$_y$—, —[$CH_2CH_2$O]$_y$—$CH_2$—, where y=1–4, —[$CH_2CH_2$N($CH_3$)]$_3$—, —($CH_2CH_2$NH)$_3CH_2CH_2$—, —$CH_2$—$CH_2$—CH($CH_3$)—NH—$CH_2$—CH($CH_3$)—, —$CH_2$CH($CH_3$)—N($CH_3$)—$CH_2$—CH($CH_3$)— or —$CH_2$—CH($CH_3$)—NH—$CH_2$—$CH_2CH_2$—.

$C_3$–$C_6$alkenyl, for example $C_3$–$C_5$alkenyl, radicals are mono- or polyunsaturated and are linear or branched. Examples are allyl, methallyl, 1,1-dimethylallyl, 1-butenyl, 3-butenyl, 2-butenyl, 1,3-pentadienyl, or 5-hexenyl, especially allyl. $C_1$–$C_4$alkoxy is linear or branched, namely, methoxy, ethoxy, propoxy, isopropoxy, n-butyloxy, sec-butyloxy, isobutyloxy, tert-butyloxy, especially methoxy, ethoxy, propoxy, isopropoxy, preferably methoxy.

$C_1$–$C_4$alkylthio is linear or branched, namely, methylthio, ethylthio, n-propylthio, i-propylthio, n-butylthio, i-butylthio, s-butylthio, t-butylthio, preferably methylthio or butylthio.

Substituted phenyl is substituted one to five times, for example once, twice or three times, especially once or twice. Substituents are, for example in position 2, 3, 4, 5 or 6, especially in position 2, 6 or 3 of the phenyl ring.

The terms "and/or" or "or/and" in the present context are meant to express that not only one of the defined alternatives (substituents) may be present, but also several of the defined alternatives (substituents) together, namely mixtures of different alternatives (substituents).

The term "at least" is meant to define "one" or "more than one", for example one or two or three, preferably one or two.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The present compounds of formula I are prepared in general by treatment of a metallated organosilyl compound (II) with a corresponding halogenoborane (III) in an appropriate solvent such as tetrahydrofuran and n-hexane:

$R_1$, $R_2$, $R_3$, $R_4$, $R_5$, $R_6$ and $R_7$ are as defined above. X is chloro or bromo, M is an alkali metal, preferably Li.

The reaction is carried out in a suitable solvent, e.g. an ether, such as tetrahydrofurane (THF) or an aliphatic hydrocarbon, such as n-hexane. For example, other aprotic solvents such as petrol ethers and aromatic hydrocarbons as well as dialkyl ethers are suitable for this reaction, too.

Usually the reaction is conducted using the educt in a molar ratio of 1:1.

The organosilyl lithium usually is prepared from lithium metal and organosilyl halide in an appropriate solvent, e.g. THF (ca. 1 mol/l). The organosilyl borane is prepared by dropwise addition of the organosilyl lithium to the halogenoborane in an appropriate solvent, e.g. n-hexane or THF (ca. 1 mol/l).

The person skilled in the art is aware of convenient reaction temperatures. The temperatures usually depend on the solvent used and generally range between 0° C. and ambient temperature.

Preparation examples of organosilyl borane educts, as used for the synthesis of the compounds according to the invention, are described in Organometallics 1995, 14, 3112–3115. The preparation of halogenoboranes is, for example described in J. Organomet. Chem. 1993, 455, 37–46.

Preference is given to the compounds of formula I, wherein $R_1$, $R_2$, and $R_3$ independently of one another are $C_1$–$C_{20}$alkyl which is unsubstituted or substituted by OH, $C_1$–$C_4$alkoxy, $C_1$–$C_4$alkylthio, phenylthio, F, Cl, Br, I, CN, $(C_1$–$C_8$alkyl)O(CO)—, $(C_1$–$C_4$alkyl)-(CO)O— or/and di($C_1$–$C_4$alkyl)amino, or $R_1$, $R_2$, and $R_3$ independently of one another are $C_3$–$C_6$alkenyl, or phenyl which is unsubstituted or substituted by OH, $C_1$–$C_4$alkoxy, $C_1$–$C_4$alkylthio, phenylthio, F, Cl, Br, I, CN, $(C_1$–$C_8$alkyl)O(CO)—, $(C_1C_4$alkyl)-(CO)O— or di($C_1$–$C_4$alkyl)amino.

In preferred compounds of formula I $R_4$, $R_5$, $R_6$, and $R_7$ independently of one another are sec-$C_3$–$C_{20}$alkyl which is unsubstituted or substituted by OH, $C_1$–$C_4$alkoxy, $C_1$–$C_4$alkylthio, phenylthio, F, Cl, Br, I, CN, $(C_1$–$C_8$alkyl)O(CO)—, $(C_1$–$C_4$alkyl)-(CO)O— or di($C_1$–$C_4$alkyl)amino.

Particularly preferred are the compounds of formula 1, wherein $R_1$, $R_2$, and $R_3$ independently of one another are $C_1$–$C_{20}$alkyl or phenyl; and $R_4$, $R_5$, $R_6$, and $R_7$ independently of one another are sec-$C_3$–$C_{20}$ alkyl.

The compounds according to the present invention can be used as photoinitiators for polymerization. The person skilled in the art generally knows how to conduct a photochemically induced polymerization. Polymers bearing organosilyl termini can be prepared by using the present compounds as photoinitiators. The polymerization usually can be carried out in bulk or in any solution at any concentration. Examples of suitable solvents are hydrocarbons such as benzene, toluene, xylene, cyclohexane; esters such as ethyl acetate, butyl acetate, amyl acetate; ketones such as acetone, methyl ethyl ketone, methyl isobutyl ketone, cyclohexanone; ethers such as tetrahydrofuran and 1,4-dioxane; alcohols such as methanol, ethanol, isobutyl alcohol, 1,2,6-hexanetriol glycerin; amides such as N,N-dimethylformamide, N-methylformamide, N,N-diethylformamide, N-methylacetamide, N,N-dimethylacetamide, N-methylpropionamide; pyrrolidones such as 1-methyl-2-pyrrolidone, pyrrolidone ε-caprolactam; glycols such as ethylene glycol, propylene glycol, butylene glycol, tri(methylene glycol), tri(ethylene glycol), hexylene glycol, di(ethylene glycol), diethylene glycol, di(propylene glycol), poly(ethylene glycol); glycol ethers such as 2-methoxyethanol, 2-ethoxyethanol, 2-(2-methoxy)ethoxy ethanol, 2-propoxyethanol, 2-butoxyethanol, di(ethylene glycol) monomethyl ether, di(ethylene glycol) monoethyl ether, di(ethylene glycol) monobutyl ether, tri(ethylene glycol) monoethyl ether, 1-methoxy-2-propanol, 1-ethoxy-2-propanol, di(propylene glycol) monomethyl ether, di(propylene glycol) monoethyl ether, tri(propylene glycol) monomethyl ether, 3-methoxy-3-methyl-1-butanol; halogenated hydrocarbon, such as chloroform or methylene chloride. The solvent may also be in the form of a mixture of two or more of the above-mentioned solvents.

Suitable monomers for the polymerization according to the invention are of formula (II),
wherein $X_1$ is —CN, —OSi($R_{8a}$)($R_{8b}$)($R_{8c}$), —$R_9$, $OR_{10}$, —$SR_{10}$, —$NR_{11}R_{12}$,
$Y_1$, $Y_2$ and $Y_3$ independently of one another are hydrogen, $C_1$–$C_4$alkyl, halogen, —CN or —(CO)$OR_{10}$; or $Y_1$ and $Y_3$ together are $C_3$–$C_7$alkylene, optionally interrupted by —O—, —S—, —CO— or —N($R_{10}$)— and optionally substituted by OH, $C_1$–$C_4$alkoxy or —COO($C_1$–$C_4$alkyl);
$X_2$ is —OSi($R_8$)$_3$, —$R_9$, —$OR_{10}$, —$SR_{10}$, —$NR_{11}R_{12}$;
$R_{8a}$, $R_{8b}$, and $R_{8c}$ independently of one another are hydrogen; $C_1$–$C_{20}$alkyl, $C_3$–$C_{12}$-alkenyl, $C_3$–$C_8$cycloalkyl, $C_4$–$C_8$cycloalkenyl, optionally any of said radicals (with the exception of hydrogen) is mono- or polysubstituted by F, Cl, Br, CN, —N($C_1$–$C_4$alkyl)$_2$, piperidino, morpholino, OH, $C_1$–$C_4$alkoxy, —OCH$_2$CH$_2$CN, —OCH$_2$CH$_2$(CO)O ($C_1$–$C_4$alkyl), —O(CO)$R_{19}$, —(CO)OH, —(CO)O ($C_1$–$C_8$alkyl), —(CO)NH($C_1$–$C_4$alkyl), —(CO)N ($C_1$–$C_4$alkyl)$_2$, —(CO)($C_1$–$C_4$alkyl) or by
or $R_8$ is 2,3-epoxypropyl, —(CH$_2$CH$_2$O)$_m$H or —(CH$_2$CH$_2$O)$_m$ $R_{10}$; or $R_8$ is phenyl, pyridinyl, biphenyl or benzoylphenyl; optionally any of said aromatic radicals is mono- or polysubstituted by halogen, $C_1$–$C_{12}$alkyl, $C_1$–$C_{12}$alkoxy, $C_3$–$C_8$cycloalkyl, —(CO)OH, or —(CO)O ($C_1$–$C_{12}$alkyl); or $R_8$ is phenyl-$C_1$–$C_3$alkyl, $OR_{10}$, —$NR_{11}R_{12}$, or —NH(CO)$R_{10}$;
$R_9$ is hydrogen, $C_1$–$C_{20}$alkyl, $C_3$–$C_{12}$-alkenyl, $C_3$–$C_8$cycloalkyl, $C_4$–$C_8$cycloalkenyl; optionally any of said radicals (with the exception of hydrogen) mono- or polysubstituted by F, Cl, Br, CN, —N($C_1$–$C_4$alkyl)$_2$, phenyl, phenoxy, piperidino, morpholino, OH, $C_1$–$C_4$alkoxy, —OCH$_2$CH$_2$CN, —OCH$_2$CH$_2$(CO)O($C_1$–$C_4$alkyl), —O(CO)$R_{10}$, —(CO)OH, —(CO)O($C_1$–$C_8$alkyl), —(CO)NH($C_1$–$C_4$alkyl), —(CO)N($C_1$–$C_4$alkyl)$_2$, —(CO)($C_1$–$C_4$alkyl) or by;
or $R_9$ is 2,3-epoxypropyl, or —(CH$_2$CH$_2$O)$_m$ H; or $R_9$ is phenyl, pyridinyl, biphenyl, benzyl or benzoylphenyl; optionally any of said aromatic radicals is mono- or polysubstituted by halogen, $C_1$–$C_{12}$alkyl, $C_1$–$C_{12}$alkoxy, $C_3$–$C_8$cycloalkyl, —(CO)OH, —(CO)O($C_1$–$C_{12}$alkyl), —O(CO)O($C_1$–$C_1$–$C_{12}$-alkyl), tetrahydropyranyloxy, tetrahydrofuranyloxy, or tetrahydrofurfuryloxy; or $R_9$ is phenyl-$C_1$–$C_3$alkyl, tetrahydropyranyl, tetrahydrofuranyl, adamantyl, camphoryl, and $R_9$ is optionally containing one or more reactive substituents of formula
$R_{10}$ is hydrogen, $C_1$–$C_{20}$alkyl, $C_3$–$C_{12}$alkenyl, $C_3$–$C_8$cycloalkyl, $C_4$–$C_8$cycloalkenyl; optionally any of said radicals (with the exception of hydrogen) is mono- or polysubstituted by F, Cl, Br, CN, —N($C_1$–$C_4$alkyl)$_2$, phenyl, phenoxy, piperidino, morpholino, OH, $C_1$–$C_4$alkoxy, —OCH$_2$CH$_2$CN, —OCH$_2$CH$_2$(CO)O($C_1$–$C_4$alkyl), —O(CO)$R_{10}$, —(CO)OH —(CO)O($C_1$–$C_8$alkyl), —(CO)NH($C_1$–$C_4$alkyl), —(CO)N($C_1$–$C_4$alkyl)$_2$, —(CO) ($C_1$–$C_4$alkyl) or by
or $R_{10}$ is 2,3-epoxypropyl, or —(CH$_2$CH$_2$O)$_m$ H; or $R_{10}$ is phenyl, pyridinyl, biphenyl, benzyl or benzoylphenyl, optionally any of said aromatic radicals is mono- or polysubstituted by halogen, $C_1$–$C_{12}$alkyl, $C_1$–$C_{12}$alkoxy, $C_3$–$C_8$cycloalkyl, —(CO)OH, —(CO)O($C_1$–$C_{12}$alkyl), —O(CO)O($C_1$–$C_{12}$-alkyl), tetrahydropyranyloxy, tetrahydrofuranyloxy, or tetrahydrofurfuryloxy; or $R_{10}$ is phenyl -$C_1$–$C_3$alkyl, tetrahydropyranyl, tetrahydrofuranyl, adamantyl, camphoryl; and $R_{10}$ is optionally containing one or more reactive substituents of formula
$R_{11}$ and $R_{12}$ independently of one another are hydrogen, $C_1$–$C_{12}$alkyl, optionally any of said radicals is substituted by OH, $C_1$–$C_4$alkoxy, CN or —(CO)O($C_1$–$C_4$alkyl), or $R_{11}$, and $R_{12}$ are $C_3$–$C_5$alkenyl, cyclohexyl, phenyl-$C_1$–$C_3$alkyl, adamantyl, camphoryl; unsubstituted phenyl or phenyl which is mono- or poly-substituted by $C_1$–$C_{12}$alkyl or halogen; or $R_{11}$ and $R_{12}$ together are $C_2$–$C_7$alkylene optionally interrupted by —O—, —S— or —N($R_{10}$)—;

$Y_4$ is hydrogen or $CH_3$;

$Z_1$ is —O— or —N($R_{10}$)—;

m is 1 or 20.

The meanings of the radicals alkyl, alkenyl, halogen, alkoxy and alkylene are as given above. $C_3$–$C_8$cycloalkyl is, for example, in particular $C_5$–$C_6$cycloalkyl. Examples are cyclopropyl, cyclobutyl, cyclopentyl, cyclohexyl, cycloheptyl, or cyclooctyl, especially cyclopentyl or cyclohexyl. $C_4$–$C_8$cycloalkenyl is mono- or polyunsaturated and is, in particular $C_5$–$C_6$cycloalkenyl. Examples are cyclobutenyl, cyclopentenyl, cyclohexenyl, cycloheptenyl, or cyclooctenyl, especially cyclopentenyl or cyclohexenyl.

Suitable monomers are hydrophilic, amphiphilic or hydrophobic.

Examples of hydrophilic monomers are (meth)acrylamide, N,N-dimethyl (meth)acrylamide, N-isopropenyl (meth)acrylamide, N-vinylformamide, (meth)acrylic acid, crotonic acid, itaconic acid, cinnamic acid, 2-hydroxyethyl (meth)acrylate, 2-hydroxypropyl (meth)acrylate, maleic acid, maleic acid anhydride, n-(l,1-dimethyl 3-oxobutyl) (meth)acrylate, 4-hydroxystyrene, 4-hydroxymethyl styrene, p-1-(2-hydroxybutyl)styrene, p-1-(2-hydroxypropyl)styrene, p-2-(2-hydroxypropyl) styrene and styrene sulfonic acid.

Examples of amphiphilic monomers or oligomers are (meth)acrylonitrile, N-(meth)acrylmorpholine, N-vinylpyrrolidone, N-vinylacetamide, N-vinyl-N-methylacetamide, vinyl methyl ether. Polyethylene glycol mono-(meth)acrylate, methoxy poly(ethylene glycol) mono-(meth)acrylate, poly(propylene glycol) mono-(meth)acrylate. N-vinylcaprolactam, N-vinylcarbazole, 4-vinylbenzyl tetrahydrofurfuryl ether and glycidyl (meth)acrylate.

Examples of hydrophobic monomers are methyl (meth)acrylate, ethyl (meth)acrylate, n-butyl (meth)acrylate, tert-butyl (meth)acrylate, 2-ethylhexyl (meth)acrylate, isobornyl (meth)acrylate, lauryl (meth)acrylate, stearyl (meth)acrylate, 1-naphtyl (meth)acrylate, 2-naphtyl (meth)-acrylate, adamantyl (meth)acrylate, styrene, 2,4,6-trimethystyrene, 2,5-dichlorostyrene, α-methoxystyrene, α-methylstyrene, 3-methylstyrene, 4-methylstyrene, 3-nitrostyrene, 4-chloromethylstyrene, 4-aminostyrene, 4-tert-butylstyrene, 4-tert-butoxycarbonyloxystyrene, 3-bromostyrene, 4-bromostyrene, 2-chlorostyrene, 3-chlorostyrene, 4-chlorostyrene, 4-cyanostyrene, 4-cyclohexylstyrene, dimethylaminomethyl-styrene, pentachlorostyrene, 4-iodostyrene, β-methoxystyrene, 2-methoxystyrene, 4-methoxystyrene, 1-vinylnaphthalene, 2-vinylnaphthalene, vinyl acetate, vinyl propionate, isobutyl vinyl ether, vinyl chloride, 4-vinylbenzyl chloride, 2-fluoroethyl (meth)acrylate, perfluorocyclohexyl (meth)acrylate, perfluorooctyl (meth)acrylate, 2,2,3,3-tetrafluoropropyl (meth)acrylate, 2,2,2-trifluoroethyl (meth)acrylate and 3-(trifluoromethyl) benzyl (meth)acrylate.

The monomers can be used alone or in any desired mixtures.

Preferred monomers are selected from the group consisting of acrylates, methacrylates and vinyl esters.

The polymerization generally is carried out in inert atmosphere in order to avoid inactivation of the generated radicals. Examples of suitable inert gases are nitrogen, helium, neon, argon and xenon.

The polymerization usually is conducted at an appropriate temperature at which the monomers can be polymerized. The temperature strongly depends on the choice of the monomer and solvent. It should be higher than the melting point of the employed monomers and solvents and lower than the boiling point of them. The temperature is generally in the range from −40° C. to 180° C., preferably from 0° C. to 100° C.

The number and weight average molecular weights of the obtained polymers can be determined by a common method such as GPC (gel permeation chromatography) measurement calibrated by the standard styrene or/and methacrylate and are in the range from 300 to 10'000'000, preferably from 500 to 1'000'000.

In accordance with the invention, the novel compounds can be used as photoinitiators for the photopolymerization of ethylenically unsaturated compounds or of mixtures which comprise such compounds.

The invention therefore also relates to photopolymerizable compositions comprising (A) at least one ethylenically unsaturated photopolymerizable compound and (B) at least one compound of formula I as described above.

The composition may comprise additionally to the component (B) at least one further photoinitiator (C), and/or further coinitiators (D) and/or other additives (E).

The photosensitivity of the novel compositions as described above in general can extend from about 200 nm to 600 nm (UV region).

Ethylenically unsaturated photopolymerizable compounds, component (A), may include one or more olefinic double bonds. They may be of low (monomeric) or high (oligomeric) molecular mass. Examples of monomers containing a double bond are alkyl or hydroxyalkyl acrylates or methacrylates, for example methyl, ethyl, butyl, 2-ethylhexyl or 2-hydroxyethyl acrylate, isobornyl acrylate, methyl methacrylate or ethyl methacrylate. Silicone acrylates are also advantageous. Other examples are acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride or vinylidene chloride.

Examples of monomers containing two or more double bonds are the diacrylates of ethylene glycol, propylene glycol, neopentyl glycol, hexamethylene glycol or of bisphenol A, and 4,4'-bis(2-acryl-oyloxyethoxy)diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl) isocyanurate.

Examples of polyunsaturated compounds of relatively high molecular mass (oligomers) are acrylisized epoxy resins, acrylisized polyesters, polyesters containing vinyl ether or epoxy groups, and also polyurethanes and polyethers. Further examples of unsaturated oligomers are unsaturated polyester resins, which are usually prepared from maleic acid, phthalic acid and one or more diols and have molecular weights of from about 500 to 3'000. In addition it is also possible to employ vinyl ether monomers and oligomers, and also maleate-terminated oligomers with polyester, polyurethane, polyether, polyvinyl ether and epoxy main chains. Of particular suitability are combinations of oligomers which carry vinyl ether groups and of polymers as described in WO 90/01512. However, copolymers of vinyl ether and maleic acid-functionalized monomers are also suitable. Unsaturated oligomers of this kind can also be referred to as prepolymers.

Particularly suitable examples are esters of ethylenically unsaturated carboxylic acids and polyols or polyepoxides, and polymers having ethylenically unsaturated groups in the chain or in side groups, for example unsaturated polyesters, polyamides and polyurethanes and copolymers thereof, alkyd resins, polybutadiene and butadiene copolymers, polyisoprene and isoprene copolymers, polymers and copolymers containing (meth)acrylic groups in side chains, and also mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic and methacrylic acid are preferred.

Suitable polyols are aromatic and, in particular, aliphatic and cycloaliphatic polyols. Examples of aromatic polyols are hydroquinone, 4,4'-dihydroxydiphenyl and 2,2-di(4-hydroxyphenyl)propane. Examples of polyepoxides are those based on the above mentioned polyols, especially the aromatic polyols, and epichlorohydrin. Other suitable polyols are polymers or copolymers containing hydroxyl groups in the polymer chain or in side groups, examples being polyvinyl alcohol and copolymers thereof, polyhydroxyalkyl methacrylates or copolymers thereof or novolak resins. Further polyols which are suitable are oligoesters having hydroxyl end groups.

Examples of aliphatic and cycloaliphatic polyols are alkylenediols having preferably 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris($\beta$-hydroxyethyl)amine, trimethylolethane, trimethylolpropane, pentaerythritol, dipentaerythritol and sorbitol.

The polyols may be partially or completely esterified with one carboxylic acid or with different unsaturated carboxylic acids, and in partial esters the free hydroxyl groups may be modified, for example etherified or esterified with other carboxylic acids.

Examples of esters are: trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetra methacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol with a molecular weight of from 200 to 1'500, or mixtures thereof.

Also suitable are the amides of identical or different, unsaturated carboxylic acids with aromatic, cycloaliphatic and aliphatic polyamines having preferably 2 to 6, especially 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-$\beta$-aminoethyl ether, diethylenetriamine, triethylenetetramine, di-($\beta$-aminoethoxy)- or di($\beta$-aminopropoxy)ethane. Other suitable polyamines are polymers and copolymers, preferably with additional amino groups in the side chain, and oligoamides having amino end groups. Examples of such unsaturated amides are methylenebisacrylamide, 1,6-hexamethylenebisacrylamide, diethylenetriaminetrismethacrylamide, bis-(methacrylamidopropoxy)ethane, $\beta$-methacrylamidoethyl methacrylate and N[($\beta$-hydroxyethoxy)ethyl]acrylamide.

Suitable unsaturated polyesters and polyamides are derived, for example, from maleic acid and from diols or diamines. Some of the maleic acid can be replaced by other dicarboxylic acids. They can be used together with ethylenically unsaturated comonomers, for example styrene. The polyesters and polyamides may also be derived from dicarboxylic acids and from ethylenically unsaturated diols or diamines, especially from those with relatively long chains of, for example 6 to 20 C atoms. Examples of polyurethanes are those composed of saturated or unsaturated diisocyanates and of unsaturated or, respectively, saturated diols.

Polybutadiene and polyisoprene and copolymers thereof are known. Examples of suitable comonomers are olefins, such as ethylene, propene, butene and hexene, (meth) acrylates, acrylonitrile, styrene or vinyl chloride. Polymers with (meth)acrylate groups in the side chain are likewise known. They may, for example, be reaction products of epoxy resins based on novolaks with (meth)acrylic acid, or may be homo- or copolymers of vinyl alcohol or hydroxyalkyl derivatives thereof which are esterified with (meth) acrylic acid, or may be homo- and copolymers of (meth) acrylates which are esterified with hydroxyalkyl (meth) acrylates.

The photopolymerizable compounds can be used alone or in any desired mixtures. Preferably used are mixtures of polyol (meth)acrylates.

Binders as well can be added to the polymerizable compositions, and this is particularly expedient when the photopolymerizable compounds are liquid or viscous substances. The quantity of binder may, for example, be 5–95%, preferably 10–90% and especially 40–90%, by weight relative to the overall solids content. The choice of binder is made depending on the field of application and on properties required for this field, such as the capacity for development in aqueous and organic solvent systems, adhesion to substrates and sensitivity to oxygen.

Examples of suitable binders are polymers having a molecular weight of about 5'000 to 2'000'000, preferably 10'000 to 1'000'000. Examples are: homo- and copolymers of acrylates and methacrylates, for example copolymers of methyl methacrylate/ethyl acrylate/methacrylic acid, poly (alkyl methacrylates), poly(alkyl acrylates); cellulose esters and cellulose ethers, such as cellulose acetate, cellulose acetobutyrate, methylcellulose, ethylcellulose; polyvinylbutyral, polyvinylformal, cyclized rubber, polyethers such as polyethylene oxide, polypropylene oxide and polytetrahydrofuran; polystyrene, polycarbonate, polyurethane, chlorinated polyolefins, polyvinyl chloride, vinyl chloride/vinylidene copolymers, copolymers of vinylidene chloride with acrylonitrile, methyl methacrylate and vinyl acetate, polyvinyl acetate, copoly(ethylene/vinyl acetate), polymers such as polycaprolactam and poly (hexamethylenadipamide), and polyesters such as poly (ethylene glycol terephtalate) and poly(hexamethylene glycol succinate) and polyimides.

The unsaturated compounds can also be used as a mixture with non-photopolymerizable, film-forming components. These may, for example, be physically drying polymers or solutions thereof in organic solvents, for instance nitrocellulose or cellulose acetobutyrate. They may also, however, be chemically and/or thermally curable (heat-curable) resins, examples being polyisocyanates, polyepoxides and melamine resins, as well as polyimide precursors. The use of heat-curable resins at the same time is important for use in systems known as hybrid systems, which in a first stage are photopolymerized and in a second stage are cross-linked by means of thermal aftertreatment.

The novel compounds according to the invention are further suitable as initiators for curing of oxidative drying systems, such as are for example described in "Lehrbuch der Lacke und Beschichtungen", Vol. 111, 296–328, Verlag W. A. Colomb in Heenemann GmbH, Berlin-Oberschwandorf (1976).

In addition to the photoinitiator the photopolymerizable mixtures may include various additives (E). Examples of these are thermal inhibitors, which are intended to prevent premature polymerization, examples being hydroquinone, hydroquinine derivatives, p-methoxyphenol, β-naphthol or sterically hindered phenols, such as 2,6-di-tert-butyl-p-cresol. In order to increase the stability on storage in the dark it is possible, for example, to use copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzy-lammonium chloride, or hydroxylamine derivatives, for example N-diethylhydroxylamine. To exclude atmospheric oxygen during the polymerization it is possible to add paraffin or similar wax-like substances which, being of inadequate solubility in the polymer, migrate to the surface in the beginning of polymerization and form a transparent surface layer which prevents the ingress of air. It is also possible to apply an oxygen-impermeable layer. Light stabilizers which can be added in a small quantity are UV absorbers, for example hydroxyphenylbenzotriazoles, in particular 2-(2'-hydroxyphenyl)benzotriazoles; hydroxyphenyl-benzophenones, in particular 2-Hydroxybenzophenones; esters of substituted or unsubstituted benzoicacids; acrylates, such as isooctyl or ethyl α-cyano-β,β-diphenyl acrylate and the like; sterically hindered amines, for example bis-(2,2,6,6-tetramethylpiperidyl) sebacate; oxalamides, for example 4,4'-dioctyloxyoxanilide; hydroxyphenyl-s-triazines, in particular 2-(2-hydroxyphenyl)-1,3,5-triazines; phosphites and phosphonites, for example triphenyl phosphite. More specific examples of Light stabilizers suitable for photopolymerizable compositions are described in DE 19907957, which herewith is incorporated by reference. The compounds can be used individually or in mixtures, with or without sterically hindered amines (HALS).

To accelerate the photopolymerization it is possible to add amines, for example triethanolamine, N-methyldiethanolamine, p-dimethylaminobenzoate or Michler's ketone. The action of the amines can be intensified by the addition of aromatic ketones of the benzophenone type. Examples of amines which can be used as oxygen scavengers are substituted N,N-dialkylanilines, as are described in EP 339841. Other accelerators, coinitiators and autoxidizers are thiols, thioethers, disulfides, phosphonium salts, phosphine oxides or phosphines, as described, for example, in EP 438123, in GB 2180358 and in JP Kokai Hei 6–68309.

It is further possible to add chain transfer agents which are customary in the art to the compositions according to the invention. Examples are mercaptanes, amines and benzothiazol.

Photopolymerization can also be accelerated by adding further photosentisizers or coinitiators (D) which shift or broaden the spectral sensitivity. These are, in particular, aromatic carbonyl compounds, for example benzophenones, thioxanthones, anthraquinones and 3-acylcoumarins, 3-(aroylmethylene)thiazolines, and derivatives of said compounds, camphor quinone, but also eosine, rhodamine and erythrosine dyes.

The curing process (in particular, of compositions which are pigmented, for example with titanium dioxide) can be assisted by adding a component which under thermal conditions forms free radicals, for example an azo compound such as 2,2'-azobis(4-methoxy-2,4-dimethylvaleronitrile), a triazene, diazo sulfide, pentazadiene or a peroxy compound, for instance a hydroperoxide or peroxycarbonate, for example t-butyl hydroperoxide, as described for example in EP 245639.

The compositions according to the invention may comprise as further additive (D) a photoreducable dye, e.g., xanthene-, benzoxanthene-, benzothioxanthene, thiazine-, pyronine-, porphyrine- or acridine dyes, and/or trihalogen-methyl compounds which can be cleaved by irradiation. Similar compositions are for example described in EP 445624.

Further customary additives, depending on the intended use, are optical brighteners, fillers, pigments, dyes, wetting agents, levelling assistants, flow improvers or adhesion promoters. In order to cure thick and pigmented coatings it is appropriate to add glass microspheres or pulverized glass fibres, as described for example in U.S. Pat. No. 5,013,768.

The compositions may also comprise dyes and/or white and colored pigments. Depending on the kind of application organic as well as anorganic pigments are used. Such additives are known to the person skilled in the art, some examples are titan dioxide pigments, e.g. of the rutile type or anatas type, carbon black Russ, zinc oxide, such as zink white, iron oxide, such as iron oxide yellow, iron oxide red, chromium yellow, chromium green, nickel titanium yellow, ultramarine blue, cobalt blue, bismuth vanadate, cadmiumy-ellow or cadmium red. Examples of organic pigments are mono- or bisazo pigments, as well as metal complexes thereof, phthalocyanine pigments, polycyclic pigments, such as perylene-, anthraquinone-, thioindigo-, chinacridone- or triphenylmethane pigments, as well as diketo-pyrrolo-pyrole-, isoindolinone-, e.g. tetrachlorisoindolinone-, isoindoline-, dioxazin-, benzimidazolone- and chinophthalone pigments. The pigments are employed alone or in combination in the compositions according to the invention. Depending on the intended use the pigments are used in amount customary in the art, for example in an amount of 1–60% by weight, or 10–30% by weight, based on the whole formulation.

The compositions may also comprise organic dyes of different classes. Examples are azo dyes, methin dyes, anthraquinone dyes or metal complex dyes. Customary concentrations are for example 0.1–20%, in particular 1–5%, based on the whole formulation.

The choice of additive is made depending on the field of application and on properties required for this field. The additives described above are customary in the art and accordingly are added in amounts which are usual in the respective application.

The invention also provides compositions comprising as component (A) at least one ethylenically unsaturated photopolymerizable compound which is emulsified or dissolved in water. Many variants of such radiation-curable aqueous prepolymer dispersions are commercially available and known in the art. A prepolymer dispersion is understood as being a dispersion of water and at least one prepolymer dispersed therein. The concentration of water in these systems is, for example, from 5 to 80% by weight, in particular from 30 to 60% by weight. The concentration of the radiation-curable prepolymer or prepolymer mixture is, for example, from 95 to 20% by weight, in particular from 70 to 40% by weight. In these compositions the sum of the percentages given for water and prepolymer is in each case 100, with auxiliaries and additives being added in varying quantities depending on the intended use. The radiation-curable, film-forming prepolymers which are dispersed in water and are often also dissolved are aqueous prepolymer dispersions of mono- or polyfunctional, ethylenically unsaturated prepolymers which are known per se, can be initiated by free radicals and have for example a content of from 0.01 to 1.0 mol of polymerizable double bonds per 100 g of prepolymer and an average molecular weight of, for example, at least 400, in particular from 500 to 10'000. Prepolymers with higher molecular weights, however, may also be considered depending on the intended application. Use is made, for example, of polyesters containing polymerizable C—C double bonds and having an acid number of not more than 10, of polyethers containing polymerizable C—C double bonds, of hydroxyl-containing reaction products of a polyepoxide, containing at least two epoxide groups per molecule, with at least one α,β-ethylenically unsaturated carboxylic acid, of polyurethane (meth) acrylates and of acrylic copolymers which contain α,β-ethylenically unsaturated acrylic radicals, as are described in EP 12339. Mixtures of these prepolymers can likewise be used. Also suitable are the polymerizable prepolymers described in EP 33896, which are thioether adducts of polymerizable prepolymers having an average molecular weight of at least 600, a carboxyl group content of from 0.2 to 15% and a content of from 0.01 to 0.8 mol of polymerizable C—C double bonds per 100 g of prepolymer. Other suitable aqueous dispersions, based on specific alkyl (meth)-acrylate polymers, are described in EP 41125, and suitable waterdispersible, radiation-curable prepolymers of urethane acrylates can be found in DE 2936039. Further additives which may be included in these radiation-curable aqueous prepolymer dispersions are dispersion auxiliaries, emulsifiers, antioxidants, light stabilizers, dyes, pigments, fillers, for example talc, gypsum, silicic acid, rutile, carbon black, zinc oxide, iron oxides, reaction accelerators, levelling agents, lubricants, wetting agents, thickeners, flatting agents, antifoams and other auxiliaries customary in paint technology. Suitable dispersion auxiliaries are water-soluble organic compounds which are of high molecular mass and contain polar groups, examples being polyvinyl alcohols, polyvinylpyrrolidone or cellulose ethers. Emulsifiers which can be used are nonionic emulsifiers and, if desired, ionic emulsifiers as well.

In certain cases it may be of advantage to use mixtures of two or more of the novel photoinitiators. It is of course also possible to use mixtures with known photoinitiators (C), for example mixtures with camphor quinone, benzophenone, benzophenone derivatives, acetophenone, acetophenone derivatives, for example α-hydroxycycloalkyl phenyl ketones or 2-hydroxy-2-methyl-1-phenyl-propanone, dialkoxyacetophenones, α-hydroxy- or α-aminoacetophenones, e.g. (4-methylthiobenzoyl)-1-methyl -1-morpholinoethane, (4-morpholinobenzoyl)-1-benzyl-1-dimethylaminopropane, 4-aroyl-1,3-dioxolanes, benzoin alkyl ethers and benzil ketals, e.g. dimethyl benzil ketal, phenylglyoxalic esters and derivatives thereof, dimeric phenylglyoxalic esters, peresters, e,g. benzophenone tetracarboxylic peresters as described for example in EP 126541, monoacyl phosphine oxides, e.g. (2,4,6-trimethylbenzoyl)diphenylphosphine oxide, bisacylphosphine oxides, bis(2,6-dimethoxy-benzoyl)-(2,4,4-trimethylpentyl)phosphine oxide, bis(2,4,6-trimethylbenzoyl)-phenylphosphine oxide, bis(2,4,6-trimethylbenzoyl)-2,4-dipentoxyphenylphosphine oxide, trisacylphosphine oxides, halomethyltriazines, e.g. 2-[2-(4-methoxy-phenyl)-vinyl]-4,6-bis-trichloromethyl-[1,3,5]triazine, 2-(4-methoxy-phenyl)-4,6-bis-trichloromethyl-[1,3,5]triazine, 2-(3,4-dimethoxy-phenyl)-4,6-bis-trichloromethyl-[1,3,-5]triazine, 2-methyl-4,6-bis-trichloromethyl-[1,3,5]triazine, hexaarylbisimidazole/coinitiator systems, e.g. orthochlorohexaphenyl-bisimidazole combined with 2-mercaptobenzthiazole, ferrocenium compounds, or titanocenes, e.g. bis(cyclopentadienyl)-bis(2,6-difluoro-3-pyrrylphenyl)titanium. Further, borate compounds can be used as coinitiators.

Where the novel photoinitiator systems are employed in hybrid systems, use is made, in addition to the novel free-radical hardeners, of cationic photoinitiators, for example peroxide compounds, such as benzoyl peroxide (other suitable peroxides are described in U.S. Pat. No. 4,950,581 column 19, lines 17–25), aromatic sulfonium-, phosphonium- or iodonium salts as described for example in U.S. Pat. No. 4,950,581, column 18, line 60 to column 19, line 10 or cyclopentadienyl-arene-iron(II) complex salts, for example ($\eta^6$-iso-propylbenzene)($\eta^5$-cyclopentadienyl)iron (II) hexafluorophosphate.

The photopolymerizable compositions generally comprise 0.05 to 20% by weight, e.g. 0.05 to 15% by weight, preferably 0.1 to 5% by weight, of the photoinitiator, based on the composition. The amount refers to the sum of all photoinitiators added, if mixtures of initiators are employed. Accordingly, the amount either refers to the photoinitiator (B) or the photoinitiators (B)+(C).

To perform the photopolymerization according to the invention suitable radiation is present, for example, in sunlight or light from artificial light sources. Consequently, a large number of very different types of light sources are employed. Both point sources and arrays ("lamp carpets") are suitable. Examples are carbon arc lamps, xenon arc lamps, medium-, high- and low-pressure mercury lamps, possibly with metal halide dopes (metal-halogen lamps), microwave-stimulated metal vapour lamps, excimer lamps, superactinic fluorescent tubes, fluorescent lamps, argon incandescent lamps, electronic flashlights, photographic flood lamps, light emitting diodes (LED), electron beams and X-rays. The distance between the lamp and the substrate to be exposed in accordance with the invention may vary depending on the intended application and the type and output of lamp, and may be, for example, from 2 cm to 150 cm. Laser light sources, for example excimer lasers, such as krypton F lasers for exposure at 248 nm are also suitable. Lasers in the visible region can also be employed. By this method it is possible to produce printed circuits in the electronics industry, lithographic offset printing plates or relief printing plates, and also photographic image recording materials.

The photopolymerizable compositions can be used for various purposes, for example as printing ink, e.g. as screen printing ink, ink for flexoprinting or offset printing, as a clear finish, as a colored finish, as a white finish, for example for wood or metal, as powder coating, as a coating material, inter alia for paper, wood, metal or plastic, as a daylight-curable coating for the marking of buildings and roadmarking, for photographic reproduction techniques, for holographic recording materials, for image recording techniques or to produce printing plates which can be developed with organic solvents or with aqueous alkalis, for producing masks for screen printing, as dental filling compositions, as adhesives, as pressure-sensitive adhesives, as laminating resins, as photoresits, e.g. etch resists, electroplating resists, or permanent resists, both liquid and dry films, as photostructurable dielectricum and as solder masks for electronic circuits, as resists to manufacture color filters for any type of display applications or to generate structures in the manufacturing process of plasma-display panels and electroluminescence displays, for the production of optical switches, optical lattices (interference lattice), light circuits, for producing three-dimensional articles by mass curing (UV curing in transparent moulds) or by the stereolithography technique, as is described, for example, in U.S. Pat. No. 4,575,330 to produce composite materials (for example styrenic polyesters, which may, if desired, contain glass fibres and/or other fibres and other auxiliaries) and other thick-layered compositions, for coating or sealing electronic components and chips, or as coatings for optical fibres, or for producing optical lenses, e.g. contact lenses or Fresnel lenses.

The compositions according to the invention are further suitable for the production of medical equipment, auxiliaries or implants.

Further the compositions according to the invention are suitable for the preparation of gels with thermotropic properties, as for example described in DE 19700064 and EP 678534.

The compositions according to the invention can also be used in dry paint film, as for example described in Paint&Coatings Industry, April 1997, 72 or Plastics World, vol. 54, no. 7, p48(5).

Accordingly, a further subject of the invention is the use of the novel compounds according to the invention for producing pigmented and non-pigmented paints and varnishes, for producing clear and pigmented aqueous dispersions, powder coatings, printing inks, printing plates, adhesives, dental filling compositions, wave-guides, optical switches, color proofing systems, color filter or color mosaique resists, glass fiber cable coating, screen printing stencils, resist materials, composite compositions, for photographic reproductions, for producing masks for screen printing, for photoresists for printed electronic circuits, for encapsulating electrical and electronic components, for producing magnetic recording materials, for producing three-dimensional objects by means of stereolithography or bulk-curing, and as image recording material, especially for holographic recording; as well as the use of a block copolymer as described above for the preparation of pigment dispersants, emulsion stabilizers, plastic elastomers, anti-shrinking agents, coatings, medical materials or imaging materials.

The novel compounds may additionally be employed as initiators for emulsion polymerizations, pearl polymerizations or suspension polymerizations, as polymerization initiators for fixing ordered states of liquid-crystalline monomers and oligomers, or as initiators for fixing dyes on organic materials.

In coating materials, use is frequently made of mixtures of a prepolymer with polyunsaturated monomers, which may additionally include a monounsaturated monomer as well. It is the prepolymer here which primarily dictates the properties of the coating film, and by varying it the skilled worker is able to influence the properties of the cured film. The polyunsaturated monomer functions as a crosslinking agent which renders the film insoluble. The monounsaturated monomer functions as a reactive diluent, which is used to reduce the viscosity without the need to employ a solvent.

Unsaturated polyester resins are usually used in two-component systems together with a monounsaturated monomer, preferably with styrene. For photoresists, specific one-component systems are often used, for example polymaleimides, polychalcones or polyimides, as described in DE 2308830.

The novel compound can also be used for the polymerization of radiation-curable powder coatings. The powder coatings can be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (for example methyl methylacrylamidoglycolate) and a photoinitiator according to the invention, similar formulations being described, for example, in the paper "Radiation Curing of Powder Coating", Conference Proceedings, Radtech Europe 1993 by M. Wittig and Th. Gohmann. The powder coatings can also contain binders, as are described, for example, in DE 4228514 and in EP 636669. Free-radically UV-curable powder coatings can also be formulated by mixing unsaturated polyester resins with solid acrylates, methacrylates or vinyl ethers and with a novel photoinitiator (or photoinitiator mixture). The powder coatings may also comprise binders as are described, for example, in DE 4228514 and in EP 636669. The UV-curable powder coatings may additionally comprise white or coloured pigments. For example, preferably rutile titanium dioxide can be employed in concentrations of up to 50% by weight in order to give a cured powder coating of good hiding power. The procedure normally comprises electrostatic or tribostatic spraying of the powder onto the substrate, for example metal or wood, melting of the powder by heating, and, after a smooth film has formed, radiation-curing of the coating with ultraviolet and/or visible light, using for example medium-pressure mercury lamps, metal halide lamps or xenon lamps. A particular advantage of the radiation-curable powder coatings over their heat-curable counterparts is that the flow time after melting the powder particles can be delayed in order to ensure the formation of a smooth, high-gloss coating. In contrast to heatcurable systems, radiation-curable powder coatings can be formulated to melt at lower temperatures without the unwanted effect of shortening their lifetime. For this reason, they are also suitable as coatings for heat-sensitive substrates, for example wood or plastics.

In addition to the novel photoinitiator the powder coating formulations may also include UV absorbers. Appropriate examples are listed above in sections 1.–8.

The novel photocurable compositions are suitable, for example, as coating materials for substrates of all kinds, for example wood, textiles, paper, ceramics, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$ to which it is intended to apply a protective layer or, by means of imagewise exposure, to generate an image.

Coating of the substrates can be carried out by applying to the substrate a liquid composition, a solution or a suspension. The choice of solvents and the concentration depend principally on the type of composition and on the coating technique. The solvent should be inert, i.e. it should not undergo a chemical reaction with the components and should be able to be removed again, after coating, in the course of drying. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

The solution is applied uniformly to a substrate by means of known coating techniques, for example by spin coating, dip coating, knife coating, curtain coating, brushing, spraying, especially by electrostatic spraying, and reverse-roll coating, and also by means of electrophoretic deposition. It is also possible to apply the photosensitive layer to a temporary, flexible support and then to coat the final substrate, for example a copper-clad circuit board, by transferring the layer via lamination.

The quantity applied (coat thickness) and the nature of the substrate (layer support) are dependent on the desired field of application. The range of coat thicknesses generally comprises values from about 0.1 $\mu$m to more than 100 $\mu$m, for example 20 mm or 0.02 to 10 cm, preferably 0.02 to 2 cm.

The invention therefore also pertains to a substrate coated with a photopolymerizable composition as described above.

The novel radiation-sensitive compositions further find application as negative resists, having a very high sensitivity to light and being able to be developed in an aqueous alkaline medium without swelling. They are suitable as photoresists for electronics (electroplating resist, etch resist, solder resist), the production of printing plates, such as offset printing plates or screen printing plates, for the production of printing formes for relief printing, planographic printing, rotogravure or of screen printing formes, for the production of relief copies, for example for the production of texts in braille, for the production of stamps, for use in chemical milling or as a microresist in the production of integrated circuits. The possible layer supports, and the processing conditions of the coating substrates, are just as varied.

The compositions according to the invention also find application for the production of one- or more-layered materials for the image recording ore image reproduction (copies, reprography), which may be uni- or polychromatic. Furthermore the materials are suitable for colour proofing systems. In this technology formulations containing microcapsules can be applied and for the image production the radiation curing can be followed by a thermal treatment. Such systems and technologies and their applications are for example disclosed in U.S. Pat. No. 5,376,459.

Substrates used for photographic information recordings include, for example, films of polyester, cellulose acetate or polymer-coated papers; substrates for offset printing formes are specially treated aluminium, substrates for producing printed circuits are copper-clad laminates, and substrates for producing integrated circuits are silicon wafers. The layer thicknesses for photographic materials and offset printing formes is generally from about 0.5 $\mu$m to 10 $\mu$m, while for printed circuits it is from 1.0 $\mu$m to about 100 $\mu$m.

Following the coating of the substrates, the solvent is removed, generally by drying, to leave a coat of the photoresist on the substrate.

The term "imagewise" exposure includes both, exposure through a photomask comprising a predetermined pattern, for example a slide, as well as exposure by means of a laser or light beam, which for example is moved under computer control over the surface of the coated substrate and in this way produces an image, and irradiation with computer-controlled electron beams. It is also possible to use masks made of liquid crystals that can be adressed pixel by pixel to generate digital images, as is, for example, described by A. Bertsch, J. Y. Jezequel, J. C. Andre in Journal of Photochemistry and Photobiology A: Chemistry 1997, 107, p. 275–281 and by K.-P. Nicolay in Offset Printing 1997, 6, p. 34–37.

Following the imagewise exposure of the material and prior to development, it may be advantageous to carry out thermal treatment for a short time. In this case only the exposed sections are thermally cured. The temperatures employed are generally 50–150° C., preferably 80–130° C.; the period of thermal treatment is in general between 0.25 and 10 minutes.

The photopolymerizable composition comprising the novel compound according to the invention can be used in color filter (color mosaique) resists.

The photocurable composition may additionally be used in a process for producing printing plates or photoresists as is described, for example, in DE 4013358. In such a process the composition is exposed for a short time to visible light with a wavelength of at least 400 nm, without a mask, prior to, simultaneously with or following imagewise irradiation.

After the exposure and, if implemented, thermal treatment, the unexposed areas of the photosensitive coating are removed with a developer in a manner known per se.

As already mentioned, the novel compositions can be developed by aqueous alkalis. Particularly suitable aqueous-alkaline developer solutions are aqueous solutions of tetraalkylammonium hydroxides or of alkali metal silicates, phosphates, hydroxides and carbonates. Minor quantities of wetting agents and/or organic solvents may also be added, if desired, to these solutions. Examples of typical organic solvents, which may be added to the developer liquids in small quantities, are cyclohexanone, 2-ethoxyethanol, toluene, acetone and mixtures of such solvents.

Photocuring is of great importance for printings, since the drying time of the ink is a critical factor for the production rate of graphic products, and should be in the order of fractions of seconds. UV-curable inks are particularly important for screen printing and offset inks.

As already mentioned above, the novel compositions are suitable for producing printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent or aqeous solutions.

Another field where photocuring is employed is the coating of metals, in the case, for example, of the coating of metal plates and tubes, cans or bottle caps, and the photocuring of polymer coatings, for example of floor or wall coverings based on PVC.

Examples of the photocuring of paper coatings are the colourless varnishing of labels, record sleeves and book covers.

Also of interest is the use of the novel compounds and photoinitiator systems for curing shaped articles made from composite compositions. The composite compound consists of a self-supporting matrix material, for example a glass fibre fabric, or alternatively, for example, plant fibres [cf. K.-P. Mieck, T. Reussmann in Kunststoffe 85 (1995), 366–370], which is impregnated with the photocuring formulation. Shaped parts comprising composite compounds, when produced using the novel compounds, attain a high level of mechanical stability and resistance. The novel compounds can also be employed as photocuring agents in moulding, impregnating and coating compositions as are described, for example, in EP 7086. Examples of such compositions are gel coat resins, which are subject to stringent requirements regarding curing activity and yellowing resistance, and fibre-reinforced mouldings, for example, light diffusing panels which are planar or have lengthwise or crosswise corrugation. Techniques for producing such mouldings, such as hand lay-up, spray lay-up, centrifugal casting or filament winding, are described, for example, by P. H. Selden in "Glasfaserverstärkte Kunststoffe", page 610, Springer Verlag Berlin-Heidelberg-New York 1967. Examples of articles which can be produced by these techniques are boats, fibre board or chipboard panels with a double-sided coating of glass fibre-reinforced plastic, pipes, containers, etc. Further examples of moulding, impregnating and coating compositions are UP resin gel coats for mouldings containing glass fibres (GRP), such as corrugated sheets and paper laminates. Paper laminates may be based on urea resins or melamine resins. Prior to production of the laminate, the gel coat is produced on a support (for example a film). The novel photocurable compositions can also be used for casting resins or for embedding articles, for example electronic components, etc. Curing usually is carried out using medium-pressure mercury lamps as are conventional in UV curing. However, there is also interest in less intense lamps, for example of the type TL 40W/03 or TL40W/05. The intensity of these lamps corresponds approximately to that of sunlight. It is also possible to use direct sunlight for curing. A further advantage is that the composite composition can be removed from the light source in a partly cured, plastic state and can be shaped, with full curing taking place subsequently.

The compositions and compounds according to the invention can be used for the production of holographies, waveguides, optical switches wherein advantage is taken of the development of a difference in the index of refraction between irradiated and unirradiated areas.

The use of photocurable compositions for imaging techniques and for the optical production of information carriers is also important. In such applications, as already described above, the layer (wet or dry) applied to the support is irradiated imagewise, e.g. through a photomask, with UV or visible light, and the unexposed areas of the layer are removed by treatment with a developer. Application of the photocurable layer to metal can also be carried out by electrodeposition. The exposed areas are polymeric through crosslinking and are therefore insoluble and remain on the support. Appropriate colouration produces visible images. Where the support is a metallized layer, the metal can, following exposure and development, be etched away at the unexposed areas or reinforced by electroplating. In this way it is possible to produce electronic circuits and photoresists.

Another application of the present invention includes various radical-based reactions in organic synthesis as described in, for example, Acc. Chem. Res. Vol. 25, 188–194 (1992). For instance, the novel compounds may be used for various reactions such as hydrosilylation of carbon-carbon multiple bond, reduction of alkyl halides, aryl halides, alkyl isocyanides, acyl halides, and so on. The novel compounds may also be used for radical based cyclization reactions as described in, for example, Tetrahedron Letters Vol. 31, 5265–5268 (1990).

The invention additionally provides compositions for producing pigmented and nonpigmented paints and varnishes, powder coatings, printing inks, e.g. screen printing inks, inks for offset- or flexo printing, printing plates, adhesives, dental compositions, waveguides, optical switches, colour proofing systems, color filter or color mosaique resists, composite compositions, glass fibre cable coatings, screen printing stencils, resist materials, electroplating resists, etch resists, solder resists, for encapsulating electrical and electronic components, for producing magnetic recording materials, for producing three-dimensional objects by means of stereolithography, and as image recording material, especially for holographic recordings, decolorizing materials, decolorizing materials for image recording materials, for image recording materials using microcapsules.

The invention further provides a coated substrate which is coated on at least one surface with a composition as described above, and describes a process for the photographic production of relief images, in which a coated substrate is subjected to imagewise exposure and then the unexposed portions are removed with a solvent. Imagewise exposure may be effected by irradiating through a mask or by means of a laser beam. Of particular advantage in this context is the laser beam exposure already mentioned above.

The examples which follow illustrate the invention in more detail. Parts and percentages are, as in the remainder of the description and in the claims, by weight, unless stated otherwise. Where alkyl radicals having more than three carbon atoms are referred to without any mention of specific isomers, the n-isomers are meant in each case.

EXAMPLE 1

Synthesis of bis(diisopropylamino) dimethylphenylsilylborane

To 80 mmol of lithium in 20 ml of tetrahydrofurane (THF) 20 mmol of dimethylphenylsilyl chloride is added dropwise. The solution is stirred for 6 h at room temperature. The dimethylphenylsilyl lithium solution thus prepared is added dropwise to a solution of chlorobis(diisopropylamino) borane (20 mmol) in n-hexane (20 ml). After stirring the solution for 12 h, the produced precipitates are filtered off. The filtrate is concentrated in vacuo to give a residue, which is distilled (130–140° C. at 0.2 mmHg) to afford bis (diisopropylamino)dimethylphenylsilylborane (5.13 g, 77% yield). The structure is confirmed by the proton and carbon nuclear magnetic resonance spectra, ($^1$H NMR, $^{13}$C NMR), as well as high resolution mass spectrometry (HRMS).

$^1$H NMR ($C_6D_6$): δ0.51 (s, 6H), 1.14 (d, J=6.8 Hz, 24H), 3.85 (hept, J=6.8 Hz, 4H), 7.15–7.32 (m, 3H), 7.62–7.70 (m, 2H); $^{13}$C NMR ($C_6D_6$): δ1.0, 25.4, 49.2, 127.9, 128.3, 134.4, 144.2; HRMS, calculated for $C_{20}H_{39}BN_2Si$ (M+1) 347.3054; found 347.3059.

EXAMPLE 2

Synthesis of bis(diisopropylamino) triphenylsilylborane

Bis(diisopropylamino)triphenylsilylborane is prepared in the same manner as the compound of example 1, however using triphenylsilyl chloride instead of dimethylphenylsilyl chloride. The compound is achieved in a yield of 48%. The Boiling point (Bp.) is 180–190° C. at 0.1 mmHg.

$^1$H NMR (C$_6$D$_6$): δ1.07 (d, J=7.0 Hz, 24H), 3.94 (hept, J=7.0 Hz, 4H), 7.15–7.29 (m, 9H), 7.80–7.92 (m, 6H); $^{13}$C NMR (C$_6$D$_6$): δ25.4, 50.2, 127.9, 128.3, 136.8, 140.2 Elementary analysis: Calculated for C$_{30}$H$_{43}$ N$_2$BSi: H, 9.21; C, 76.57; N, 5.95; found: H, 9.40; C, 76.30; N, 5.88.

EXAMPLE 3

Photopolymerization Reaction

A solution of the photoinitiator (0.1 mmol) in 1.0 ml of monomer and 2.0 ml of benzene is irradiated under nitrogen atmosphere for 1.5 hr with a high-pressure mercury lamp. During irradiation the samples are kept at ambient temperature in a water bath. After volatile compounds are removed under reduced pressure, the reaction mixture is poured into 50 ml of methanol. Produced precipitates are collected by filtration and dried. The molecular weight is determined by GPC analysis (gel permeation chromatography). The initiator and monomer used as well as the yield and properties of the prepared polymer are shown in table 1 below. It is elucidated by $^1$H NMR study that each polymer contains an organosilyl terminal.

What is claimed is:

1. Compounds of formula I

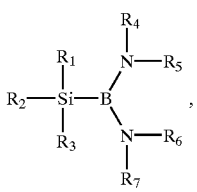

(I)

$R_1$, $R_2$, and $R_3$ independently of one another are hydrogen; C$_1$–C$_{20}$alkyl which is unsubstituted or substituted by OH, C$_1$–C$_4$alkoxy, C$_1$–C$_4$alkylthio, phenylthio, F, Cl, Br, I, CN, (C$_1$–C$_8$-alkyl)O(CO)—, (C$_1$–C$_4$alkyl)-(CO)O— or/and di(C$_1$–C$_4$alkyl)amino; or $R_1$, $R_2$, and $R_3$ independently of one another are C$_3$–C$_6$alkenyl; or are phenyl which is unsubstituted or substituted by OH, C$_1$–C$_4$alkoxy, C$_1$–C$_4$alkylthio, phenylthio, F, Cl, Br, I, CN, (C$_1$–C$_8$alkyl)O(CO)—, (C$_1$–C$_4$alkyl)-(CO)O— or/and di(C$_1$–C$_4$alkyl)amino; or $R_1$ and $R_2$ together are C$_2$–C$_9$alkylene, o-xylylene, 2-butenylene, C$_3$–C$_9$oxaalkylene or C$_3$–C$_9$azaalkylene;

$R_4$, $R_5$, $R_6$, and $R_7$ independently of one another are sec-C$_3$–C$_{20}$alkyl, tert-C$_4$–C$_{20}$alkyl or phenyl wherein these radicals are unsubstituted or substituted by OH, C$_1$–C$_4$alkoxy, C$_1$–C$_4$alkylthio, phenylthio, F, Cl, Br, I, CN, (C$_1$–C$_8$alkyl)O(CO)—, (C$_1$–C$_4$alkyl)-(CO)O— or/and di(C$_1$–C$_4$alkyl)amino;

or $R_4$ and $R_5$, and/or $R_6$ and $R_7$ together are C$_2$–C$_9$alkylene, o-xylylene, 2-butenylene, C$_3$–C$_9$oxaalkylene or C$_3$–C$_9$azaalkylene, or $R_4$ and $R_6$, and/or $R_5$ and $R_7$ together are branched C$_2$–C$_9$alkylene, o-xylylene, 2-butenylene, C$_3$–C$_9$oxaalkylene or C$_3$–C$_9$azaalkylene.

2. Compounds of formula I according to claim 1, wherein $R_1$, $R_2$, and $R_3$ independently of one another are C$_1$–C$_{20}$alkyl which is unsubstituted or substituted by OH, C$_1$–C$_4$alkoxy, C$_1$–C$_4$alkylthio, phenylthio, F, Cl, Br, I, CN, (C$_1$–C$_8$alkyl)O(CO)—, (C$_1$–C$_4$alkyl)-(CO)O— or/and di(C$_1$–$_4$alkyl)amino, or $R_1$, $R_2$, and $R_3$ independently of one another are C$_3$–C$_6$alkenyl, or phenyl which is unsubstituted or substituted by OH, C$_1$–C$_4$alkoxy, C$_1$–C$_4$alkylthio, phenylthio, F, Cl, Br, I, CN, (C$_1$–C$_8$alkyl)O(CO)—, (C$_1$–C$_4$alkyl )-(CO)O— di(C$_1$–C$_4$alkyl)amino.

3. Compounds of formula I according to claim 1, wherein $R_4$, $R_5$, $R_6$, and $R_7$ independently of one another are sec-C$_3$–C$_{20}$alkyl which is unsubstituted or substituted by OH, C$_1$–C$_4$alkoxy, C$_1$–C$_4$alkylthio, phenylthio, F, Cl, Br, I, CN, (C$_1$–C$_8$alkyl)O(CO)—, (C$_1$–C$_4$alkyl)-(CO)O— or di(C$_1$–C$_4$alkyl)amino.

4. Compounds of formula I according to claim 1, wherein $R_1$, $R_2$, and $R_3$ independently of one another are C$_1$–C$_{20}$alkyl or phenyl; and $R_4$, $R_5$, $R_6$, and $R_7$ independently of one another are sec-C$_3$–C$_{20}$ alkyl.

5. Process for the preparation of compounds of formula I according to claim 1, wherein a metallated organosilyl compound of formula II is reacted with a halogenoborane of formula III wherein $R_1$, $R_2$, $R_3$, $R_4$, $R_5$, $R_6$ and $R_7$ are as defined in claim 1 for formula I;

X is chloro or bromo; and

M is Na, K or Li.

6. Photopolymerizable composition comprising (A) at least one ethylenically unsaturated photopolymerizable compound and (B) at least one compound of formula I according to claim 1.

7. Photopolymerizable composition according to claim 6 additionally to the component (B) comprising at least one further photoinitiator (C), and/or further coinitiators (D) and/or other additives (E).

8. A method for the photopolymerisation of compounds having ethylenically unsaturated double bonds, wherein a composition according to claim 6 is irradiated with light in a wavelength range of from 200 to 600 nm.

9. Method according to claim 8 for producing pigmented and nonpigmented paints and varnishes, powder coatings, printing inks, screen printing inks, inks for offset- or flexo printing, printing plates, adhesives, dental compositions, waveguides, optical switches, color proofing systems, color filter or color mosaique resists, composite compositions, glass fibre cable coatings, screen printing stencils, resist materials, electroplating resists, etch resists, solder resists, for encapsulating electrical and electronic components, for producing magnetic recording materials, for producing three-dimensional objects by means of stereolithography, and as image recording material, image recording material for holographic recordings, decolorizing materials, decolorizing materials for image recording materials, for image recording materials using microcapsules.

10. A coated substrate coated on at least one surface with a composition according to claim 6.

11. A method for the photographic production of relief images, wherein a substrate coated with a composition according to claim 6 is exposed imagewise and then the unexposed areas are removed using a solvent.

* * * * *